(12) United States Patent
Hand et al.

(10) Patent No.: US 7,014,817 B1
(45) Date of Patent: Mar. 21, 2006

(54) DISPOSABLE REMOTE ZERO HEADSPACE EXTRACTOR

(75) Inventors: Julie J. Hand, Idaho Falls, ID (US); Mark P. Roberts, Arco, ID (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 220 days.

(21) Appl. No.: 09/966,568

(22) Filed: Sep. 27, 2001

(51) Int. Cl.
*B01L 11/00* (2006.01)
*G01N 1/18* (2006.01)

(52) U.S. Cl. ...................... 422/101; 436/177
(58) Field of Classification Search ............... 422/101, 422/102, 103, 241, 243, 262; 436/177
See application file for complete search history.

(56) References Cited

U.S. PATENT DOCUMENTS

| | | | |
|---|---|---|---|
| 3,138,299 A * | 6/1964 | Staunton | 222/207 |
| 3,223,619 A * | 12/1965 | Calmon et al. | 210/667 |
| 4,376,392 A | 3/1983 | Beitel | |
| 4,453,927 A * | 6/1984 | Sinko | 604/513 |
| 4,493,792 A | 1/1985 | Graf, Jr. | |
| 5,604,320 A | 2/1997 | Boyd et al. | |
| 5,607,234 A * | 3/1997 | Ray et al. | 366/214 |
| 5,618,997 A | 4/1997 | Owens et al. | |
| 6,820,780 B1 * | 11/2004 | Forsman et al. | 224/148.2 |

* cited by examiner

*Primary Examiner*—Jill Warden
*Assistant Examiner*—Paul S. Hyun
(74) *Attorney, Agent, or Firm*—Joy Alwan; Thomas G. Anderson; Paul A. Gottlieb

(57) ABSTRACT

The remote zero headspace extractor uses a sampling container inside a stainless steel vessel to perform toxicity characteristics leaching procedure to analyze volatile organic compounds. The system uses an in line filter for ease of replacement. This eliminates cleaning and disassembly of the extractor. All connections are made with quick connect fittings which can be easily replaced. After use, the bag can be removed and disposed of, and a new sampling container is inserted for the next extraction.

16 Claims, 3 Drawing Sheets

US 7,014,817 B1

DISPOSABLE REMOTE ZERO HEADSPACE EXTRACTOR

The United States Government has rights in this invention pursuant to Contract No. DE-AC07-841D12435 between the United States Department of Energy and WINCO. Bechtel BWXT Idaho, LLC is the successor contractor to WINCO.

BACKGROUND OF THE INVENTION

Zero headspace extractors are used to perform the EPA toxicity characteristic leaching procedure to analyze volatile organic compounds. Commercially available zero headspace extractors all use stainless steel cylinders which must be cleaned and o-rings that are susceptible to decomposition. The sample is in contact with the vessel, therefore the extractor must be disassembled, cleaned and reassembled after each extraction. This increases the amount of labor required for each extraction and makes the zero head space extractor impractical for use with highly radioactive samples. These must be handled with manipulators, which are difficult to use and provides a greater opportunity for error.

U.S. Pat. Nos. 4,864,877 and 4,974,456 (both to Ortiz et al.) disclose zero headspace devices. These patents, which have related disclosures, the latter being a divisional of the former, disclose zero-headspace sampling containers intended to meet EPA sampling requirements for liquids, and not for multi phase samples, such as solvent-treated soil samples. Ortiz et al. do not disclose filtration means to retain sediment and do not disclose pressurized containers.

U.S. Pat. Nos. 5,470,535 and 5,607,234 relate to extractor vessels designed for agitating a sample mixture comprising a solids-containing sample and an extraction liquid, which include a separator or filtration means through which the sample mixture can be discharged under pressure. None of the constructions of these prior patents is suitable for meeting the objects of the present invention.

SUMMARY OF THE INVENTION

The instant invention is a remote zero headspace extractor. The remote zero headspace extractor uses a sampling container in combination with a pressure vessel or a stainless steel canister. In addition, it uses an in line filter for ease of replacement. All connections are made with quick connect fittings which allows a quick and less costly replacement of all parts. After use, the sampling container can be removed and disposed of, and a new sampling container inserted for the next extraction.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

It is an object of the invention to provide a zero headspace extractor for use with highly radioactive samples.

It is another object of the invention to reduce the amount of labor necessary for each sample extraction process.

An additional object is to provide a remote zero head space extractor having a disposable sampling container.

To achieve the foregoing and other objects and in accordance with the purpose of the present invention, as embodied and broadly described herein, the invention may comprise a sampling container inside a stainless steel container or a pressure vessel which eliminates the need for cleaning and the disassembly of the extractor.

BRIEF DESCRIPTION OF THE DRAWINGS

The accompanying drawings, which are incorporated in and form part of the specification, illustrate an embodiment of the of the present invention and together with the description, serve to explain the principles of the invention. In the drawings.

DETAILED DESCRIPTION OF THE INVENTION

Figure 1:
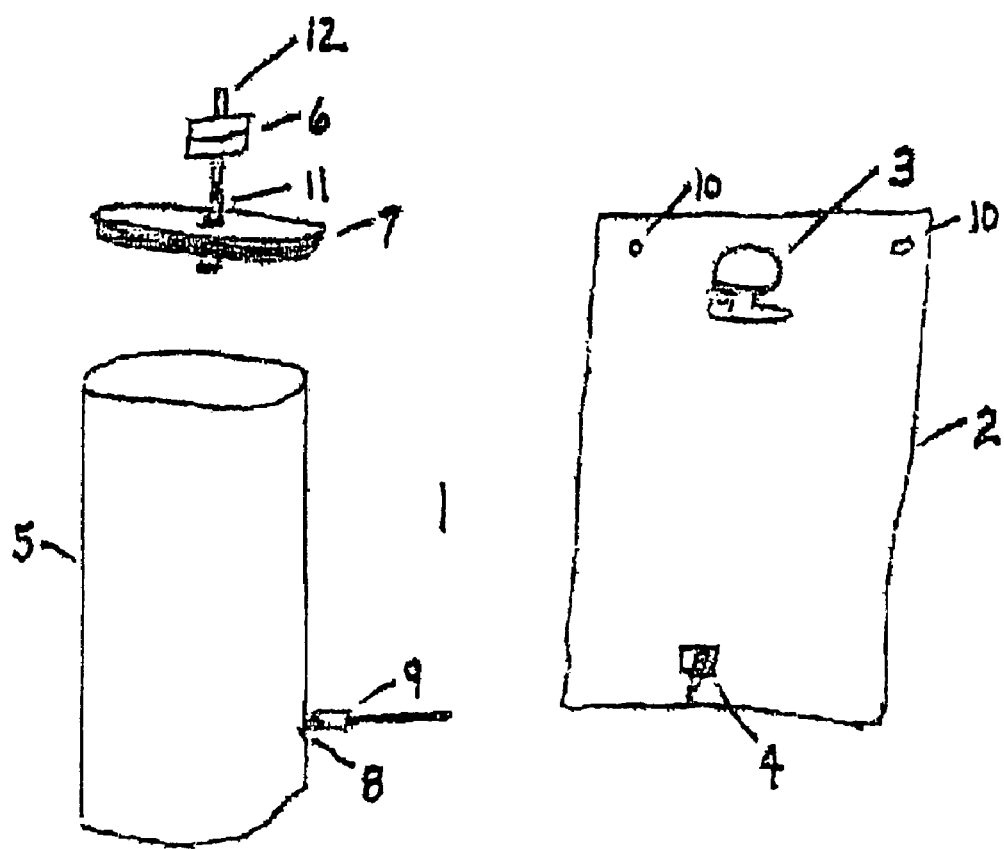
FIG. 1 shows an embodiment of the invention.

Referring to FIG. 1, The remote extraction system (1) consists of a sampling container (2), custom-designed with a wide mouth screw cap (3) at one end, and a quick connect fitting (4) at the other, a stainless steel pressure vessel (5), and an in-line filter (6). The stainless steel pressure vessel (5) has a screw top lid (7). The body of the pressure vessel (5) has a bulkhead quick connect fitting (8) which is adapted to fit a gas line (9). The extracts are collected in the sampling container (2) consisting of a tedlar bag equipped with a quick connect fitting or a glass syringe having a quick-connect fitting (4) at one end and a wide mouth opening and cap (3) at the other. Eyelets (10) are provided so that may be placed on a rack (not shown) and inserted into the pressure vessel (5). The system is designed to fit into commercially available TCLP agitators.

In operation, the sample and extraction fluid is introduced into the tedlar bag (2) through the wide mouth screw cap (3). The pressure vessel (5) is opened and the sealed, zero headspace tedlar bag (2) is placed inside the vessel (5) with the quick connect fitting (4) attached to the quick connect fitting (11) inside the lid (7). The lid (7) of the pressure vessel (5) is closed and sealed. The gas line (9) is attached to the quick-connect fitting (8) at the base of the pressure vessel (5) allowing the gas flow to be started. Any gas or liquid under pressure can be used to pressurize the vessel. An in-line filter (6) with a quick-connect fitting (12) is attached to the lid (7) of the pressure vessel (5). The gas flow will compress the tedlar bag (2) inside the pressure vessel (5) until liquid is seen at the fitting (11). The gas line (9) is disconnected and the quick connect fitting (12) on the downstream side of the filter (6) is removed maintaining pressure inside the pressure vessel (5).

The pressure vessel (5) is placed in a rotator and extracted for 18 hours. The pressure vessel (5) is removed from the rotator and placed upside-down on a rack. A second tedlar bag with a quick connect fitting (not shown) is attached to the fitting on the downstream side of the filter (6) and the gas line (9) attached to the fitting (8) on the side of the pressure vessel (5). Gas is introduced to generate pressure inside the vessel (5) and to compress the bag and force the extract into the second tedlar bag for collection.

Figure 2:
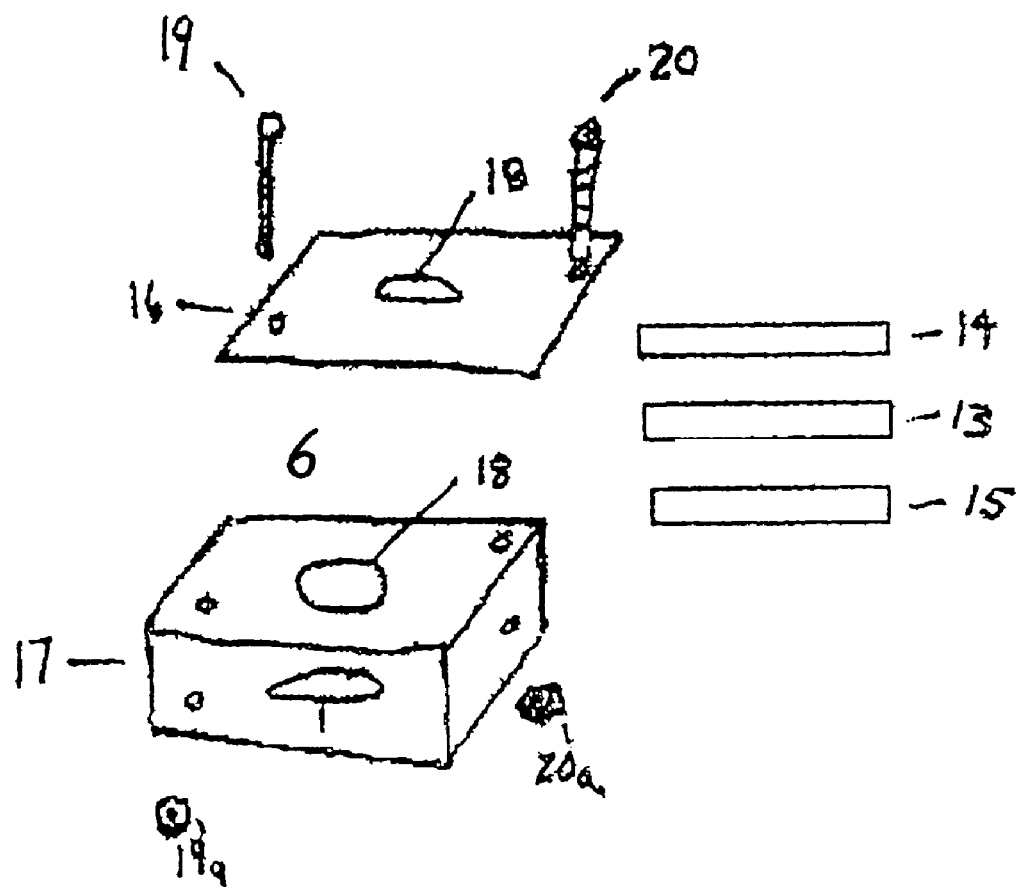
FIG. 2 shows a detail of the filter system.

As shown in FIG. 2, the filter (6) consists of a glass filter (13) sandwiched between two stainless steel screens (14, and 15) and inserted inside a two Teflon blocks (16, and 17). The Teflon blocks have centered bore holes (18) approximately ¼ inch in diameter. The filter (12) is held together by two screw and nut (19, and 20) combinations.

Figure 3:
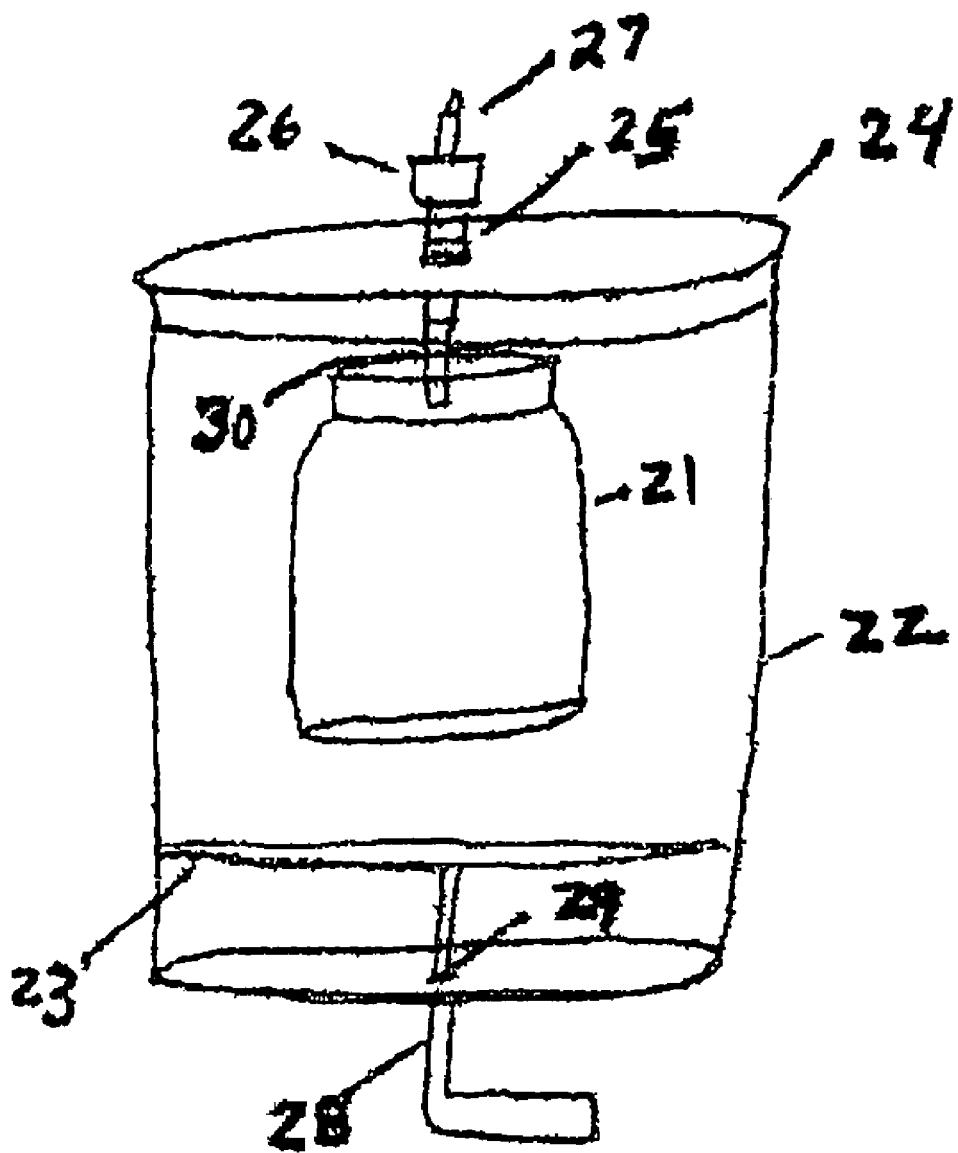
FIG. 3 shows a second embodiment of the invention.

FIG. 3 shows another embodiment of the invention, the sampling container (21) is a Teflon bottle (21). The stainless steel canister (22) is equipped with a wide mouth lid (24) that is either screwed on or acts as a flip top. The lid (24) has a quick connect fitting (25) that allows the Teflon bottle (21) has a fitting (30) to connect with upstream side of the filter (26). A second quick connect fitting (27) is mouth lid (24) that is either screwed on or acts as a flip top. The lid (24) has a quick connect fitting (25) that allows the Teflon bottle (21) with a fitting (30) to connect with an upstream side of the filter (26). A second quick connect fitting (27) is attached to the down stream side of the filter (26). The canister (22) is adapted to receive a manual piston (23). A threaded opening (29) in the canister (22) is fitted with the manual piston (23), whereby as the threaded piston rod (28) is turned pressure is asserted on the Teflon bottle (21) to remove the extract from the Teflon bottle (21) into a tedlar bag or bottle. A thread or cord can be tied around the bottle (21) so that as the piston (23) compresses the bottle (21), the bottle (21) compresses in a uniform manner.

The foregoing description of the preferred embodiment of the invention has been presented for purposes of illustration and description. It is not intended to be exhaustive or to limit the invention to the precise form disclosed, and obviously many modifications and variations are possible in light of the above teaching.

The embodiments of the invention in which an exclusive property or privilege is claimed are defined as follows:

1. An apparatus for the extraction of organic compound comprising:
    a pressure vessel having a top, a bottom, and side creating a pressurized chamber;
    an incoming sample line with an inline filter attached to the top of the pressure vessel by means of a first quick connect fitting;
    a sampling container inserted in the pressure vessel, wherein said sampling container is a bag with a second quick fitting in fluid communication with said first quick connect fitting to allow organic compounds to flow from the sampling container through the top of the pressure vessel, the sampling container further comprising a wide mouth opening with a cap on the end opposite the second quick fitting, and eyelet openings to attach the sampling container to a rack insertible in the pressure vessel; and, a gas line attached to the side of the pressure vessel by a third quick connect fitting to pressurize the pressure vessel.

2. An apparatus for the extraction of organic compounds as recited in claim 1 wherein said filter comprises:
    a glass screen positioned between a first and second stainless steel mesh, creating a sandwich arrangement;
    first and second polytetrafluoroethylene blocks encasing said sandwich arrangement, and each of said first and second blocks having centered bore holes allowing fluid flow through said first and second blocks.

3. An apparatus for the extraction of organic compounds as recited in claim 1 wherein the sampling container is comprised of a polyvinylfluoride film and wherein the wide mouth opening has a cap in a threaded connection to the sampling container.

4. The apparatus as recited in claim 1 wherein said pressure vessel is constructed of stainless steel.

5. A method of zero headspace extracting of organic compounds comprising the steps of:
    (a) sampling said organic compound and placing said organic compound in a sampling container;
    (b) pressurizing said sampling container inside a pressure vessel having a top, a bottom and sidewalls; the top having an opening with a first quick connect fitting having an upflow and downflow side affixed, the sidewalls having an opening with a second quick connect fitting having an upflow and downflow side affixed, said top being removably attached to said sidewalls creating a pressurized chamber in said pressure vessel; the sampling container having a third quick connect fitting connected to the upflow side of said first quick connect fitting of said pressure vessel; pressurizing said sample container being accomplished by connecting a pressure line to said second quick connect fitting and introducing a pressure fluid to said pressurized chamber;
    (c) rotating said pressure vessel and sampling container;
    (d) pressurizing said sampling container; and
    (e) filtering said organic compound into a second sampling container, wherein the filter comprises a glass screen positioned between a first and second stainless steel mesh creating a sandwich arrangement, a first and second polytetrafluoroethylene block encasing the sandwich arrangement, each block having a centered bore hole allowing fluid flow through the first and second block.

6. The method as recited in claim 5 wherein said step of pressurizing further comprises pressurizing said pressurized chamber until said organic compound is visible at said first quick connect fitting.

7. The method as recited in claim 5 wherein said step of rotating said pressure vessel and sampling container further comprises placing said pressure vessel in a rotator and pressure being extracted for 18 hours.

8. The method as recited in claim 5 wherein said step of pressurizing said sampling container further comprises reintroducing a pressurizing fluid into said pressurized chamber.

9. The method as recited in claim 8, wherein said step of filtering said organic compound into a second sampling container further comprises attaching a second sampling container to said filter at a fifth quick connect fitting whereby when said pressurized fluid is reintroduced into said pressurized chamber said organic compound flows through said filter into said second sampling container.

10. The method as recited in claim 5 wherein said sampling container is polyvinylfluoride film bag having said third quick connect fitting on one end of the bag and a wide mouth opening with a threaded cap on the other end of the bag.

11. A method of zero headspace extracting of organic compounds comprising the steps of:
    (a) sampling said organic compound and placing said organic compound in a sampling container;
    (b) pressurizing said sampling container inside a pressure vessel, wherein the pressure vessel is a stainless steel canister having a top, a bottom and sidewalls; the top having an opening with a first quick connect fitting having an upflow and downflow side affixed, said top being removably attached to said sidewalls creating a pressurized chamber in said pressure vessel, the bottom having an opening with a piston inserted and in contact with said sampling container;
    (c) rotating said pressure vessel and sampling container;
    (d) pressurizing said sampling container; and
    (e) filtering said organic compound into a second sampling container, wherein the filter comprises a glass screen positioned between a first and second stainless steel mesh creating a sandwich arrangement, a first and second polytetrafluoroethylene block encasing the sandwich arrangement, each block having a centered bore hole allowing fluid flow through the first and second block.

12. The method as recited in claim 11 wherein said step of pressurizing said sampling container inside a pressure vessel further comprises tying a cord or string around said sampling container and operating said piston to compress said sampling container in a uniform manner until said organic compound is visible at said first quick connect fitting.

13. The method as recited in claim 6 wherein said sampling container is a polytetrafluoroethylene bottle.

14. An apparatus for the extraction of organic compound comprising: a pressure vessel having a top, a bottom, and side creating a pressurized chamber; an incoming sample line with an inline filter attached to the top of the pressure vessel by means of a first quick connect fitting; a sampling container inserted in the pressure vessel, wherein the sampling container is a bottle having a wide mouth opening and a lid, the lid having a fifth quick connect fitting in communication with said first quick connect fitting to allow organic compounds to flow from said bottle through said top.

15. The apparatus as recited in claim 14 wherein said pressure vessel has an opening at the bottom with a piston inserted allowing manual operation of said piston from outside said pressure vessel.

16. The apparatus as recited in claim 14 wherein said sampling container is a polytetrafluoroethylene bottle.

* * * * *